United States Patent [19]

Barnish et al.

[11] 4,243,672
[45] Jan. 6, 1981

[54] 5-SUBSTITUTED 2-PYRROLEGLYOXYLIC ACIDS, 5-SUBSTITUTED 2-PYRROLYLGLYCINES AND DERIVATIVES THEREOF

[75] Inventors: Ian T. Barnish, Ramsgate; Peter E. Cross, Canterbury; Roger P. Dickinson, Dover, all of England

[73] Assignee: Pfizer Inc., New York, N.Y.

[21] Appl. No.: 70,396

[22] Filed: Aug. 28, 1979

[30] Foreign Application Priority Data

Aug. 30, 1978 [GB] United Kingdom ............... 34985/78
Feb. 1, 1979 [GB] United Kingdom ............... 03635/79

[51] Int. Cl.$^3$ ................. C07D 207/333; A61K 31/40
[52] U.S. Cl. ............................. 424/274; 260/326.2; 260/326.47
[58] Field of Search ................ 260/326.2, 326.47; 424/274

[56] References Cited

U.S. PATENT DOCUMENTS

| | | | |
|---|---|---|---|
| 3,202,654 | 8/1965 | Perron et al. | 260/326.2 |
| 3,920,730 | 11/1975 | Gleason et al. | 260/326.12 R |
| 3,994,954 | 11/1976 | Gleason et al. | 260/326.46 |
| 4,125,537 | 11/1978 | Carmosin | 260/326.2 |
| 4,148,920 | 4/1979 | Barnish et al. | 424/309 |

OTHER PUBLICATIONS

Neurath et al; Chem. Abs., vol. 72: 9744sw (1970).
Birchall et al; Chem. Abs., vol. 74:141434j (1971).
Treims et al; Chem. Abs., vol. 70: 96526v (1969).
Nenitzcscu et al; Chem. Abs., vol. 53: 17092$^d$ (1958).
Archibald et al; Chem. Abs., vol. 67: 99934a (1967).
Ingraffia; Chem. Abs., vol. 29:2163$^8$ (1934).
Fischer et al; Chem. Abs. 00125: 3008 (1931).
Archibald et al; Chem. Abs., vol. 71:81414d (1969).

Oddo et al; Chem. Abs., vol. 15: 2096 (1921).

*Primary Examiner*—Mary C. Lee
*Attorney, Agent, or Firm*—Connolly and Hutz

[57] ABSTRACT

5-Substituted 2-pyrroleglyoxylic acids, L- and DI-5-substituted 2-pyrrolylglycines and their derivatives of the formulae

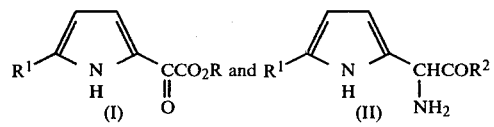

and pharmaceutically acceptable cationic and acid addition salts thereof, wherein R is hydrogen or alkyl having from one to four carbon atoms;

$R^1$ is alkyl or alkylthio having one to ten carbon atoms, alkenyl having from three to six carbon atoms, cycloalkylthio having from five to seven carbon atoms or $AR^3$ where A is a member bonded to the pyrrole ring and is alkylene or alkylenethio having from one to four carbon atoms or alkenylene having from two to four carbon atoms and $R^3$ is cycloalkyl having from three to seven carbon atoms, cycloalkenyl having from five to seven carbon atoms or $C_6H_4R^4$ where $R^4$ is H, F, Cl, Br, I, alkyl or alkoxy, the latter two groups each having from one to four carbon atoms;

$R^2$ is hydroxy, alkoxy having from one to four carbon atoms or amino; are useful in treatment of diseases and conditions which are characterized by reduced blood flow, reduced oxygen availability or reduced carbohydrate metabolism in the cardiovascular system.

21 Claims, No Drawings

5-SUBSTITUTED 2-PYRROLEGLYOXYLIC ACIDS, 5-SUBSTITUTED 2-PYRROLYLGLYCINES AND DERIVATIVES THEREOF

BACKGROUND OF THE INVENTION

1. Field of the Invention

The invention relates to novel pyrrolylketo and pyrrolylamino acids, esters and amides of the formulae (I) and (II) as defined herein and pharmaceutically acceptable salts thereof, pharmaceutical compositions thereof and their use in treating diseases and conditions of mammalian subjects, including humans, which are characterized by reduced blood flow, reduced oxygen availability or reduced carbohydrate metabolism in the cardiovascular system of the subject; such conditions include ischaemic heart disease (particularly angina pectoris and myocardial infarction) and cardiac failure.

2. Description of the Prior Art

2-Pyrroleglyoxylic acid and 2-pyrrolylglycine [alpha-amino-(2-pyrrolyl)acetic acid]and certain esters and amides thereof are known compounds. The former are disclosed by Oddo, Gazz. chim ital., 50, 258 (1920); Chem. Abstr., 15, 2096 (1921) and in U.S. 3,202,654. The latter reference also discloses alpha-amino-(2-pyrrolyl)acetic acid and the use of these compounds as intermediates for preparing penicillins. 2-Pyrroleglyoxylic acid ethyl ester is disclosed in South African Pat. No. 69 01,243; Chem. Abstr., 72, 97445W (1970) as a flavor enhancing agent for tobacco.

U.S. Pat. Nos. 3,920,730; 3,994,954 and 4,108,854 disclose N-acyl-alpha-heteroaromatic glycines, including N-acyl-2-pyrrolylglycines unsubstituted in the pyrrole moiety, in which the N-acyl group is an amino protecting group. These compounds are disclosed as being useful intermediates for the preparation of penicillins, and cephalosporins.

No pharmaceutical use for either 2-pyrroleglyoxylic acid, the corresponding alpha-amino acid or their derivatives are known.

In U.S. Pat. No. 4,148,920 L- and DL-phenylglycines of the formula

where $R_1$ is hydrogen or methyl and $R_2$ is $NH_2$, OH or completes a carboxylic ester group are disclosed as useful in treating diseases and conditions characterized by reduced blood flow, oxygen availability or reduced carbohydrate metabolism in the cardiovascular system. The D-isomers are disclosed as inactive.

SUMMARY OF THE INVENTION

The present invention provides novel 5-substituted pyrrolglycoxylic acids and 5-substituted L- and DL-2-pyrrolylglycines of the formulae I and II, respectively.

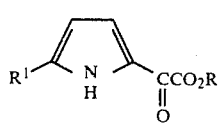

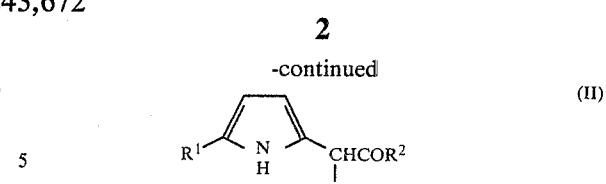

In the compounds of formula (I), R is hydrogen or alkyl having from one to four carbon atoms; $R^1$ is a member selected from the group consisting of alkyl and alkylthio each having from one to ten carbon atoms, alkenyl having from three to six carbon atoms, cycloalkylthio having from five to seven carbon atoms and $AR^3$ where A is a member bonded to the pyrrole ring and is selected from the group consisting of alkylene and alkylenethio each having from one to four carbon atoms and alkenylene having from two to four carbon atoms and $R^3$ is a member selected from the group consisting of cycloalkyl having from three to seven carbon atoms, cycloalkenyl having from five to seven carbon atoms and $C_6H_4R^4$ where $R^4$ is a member selected from the group consisting of H, F, Cl, Br, I and alkyl and alkoxy each having from one to four carbon atoms; and pharmaceutically acceptable cationic salts thereof.

Pharmaceutically acceptable cationic salts of the compounds of formula (I) include pharmaceutically acceptable metal, ammonium and amine salts of the carboxylic acid of formula (I).

Pharmaceutically acceptable metal salts include the sodium, potassium and calcium salts. Pharmaceutically acceptable amine salts include salts with arginine, N-methylglucamine and choline.

The compounds of formula (II) are pharmaceutically acceptable bioprecursors of the above compounds of formula (I). By pharmaceutically acceptable bioprecursor is meant a compound having a structural formula different from formula (I) but which, upon administration, is converted in the patient's body to a compound of formula (I).

In the compounds of formula (II), $R^1$ is as defined above for compounds of formula (I), and $R^2$ is hydroxy, amino or alkoxy having from one to four carbon atoms. Also included in the invention are the pharmaceutically acceptable cationic and acid addition salts of compounds of formula (II). The compounds and salts of formula (II) are active by virtue of their metabolism in vivo to produce the compounds of formula (I) and the amide of formula (II) where $R^2$ is amino, in particular, has advantages in use because of its better solubility properties.

Compounds of formula (II) wherein $R^2$ is hydroxy form cationic salts including the pharmaceutically acceptable metal, ammonium and amine salts defined above.

Pharmaceutically acceptable salts of compounds of the formula (II) include addition salts with acids containing pharmaceutically acceptable anions, e.g., the hydrochloride, the hydrobromide, sulphate or bisulphate, phosphate or acid phosphate, acetate, maleate, fumarate, succinate, lactate, tartrate, citrate, gluconate, sacharate and p-toluenesulfonate salts.

The L-form is the preferred form of the compounds of formula (II), the D- form being substantially inactive. It will therefore be appreciated that compounds of formula (II) derived from L-pyrrolylglycine will be substantially more active than those derived from the racemic (DL) form.

Especially preferred compounds of formulae (I) and (II) are those wherein $R^1$ is a member selected from the group consisting of alkyl having from four to six carbon atoms, cycloalkylmethyl having from three to six carbon atoms in said cycloalkyl group, 2-cyclohexylethyl and 2-cyclopentylethyl. Particularly preferred values of $R^1$ are straight chain alkyl having from four to six carbon atoms, 2-(cyclopent-2-enyl)ethyl, cyclopropylmethyl, 2-cyclohexylethyl and cyclopentylmethyl. Most particularly preferred compounds of the invention are:

2-(5-cyclopropylmethyl-2-pyrrolyl)glyoxylic acid,
2-(5-n-butyl-2-pyrrolyl)glyoxylic acid,
2-(5-n-amyl-2-pyrrolyl)glyoxylic acid,
2-(5-n-hexyl-2-pyrrolyl)glyoxylic acid,
2-[5-(2-cyclohexyl)ethyl-2-pyrrolyl]glyoxylic acid,
2-(5-cyclohexylmethyl-2-pyrrolyl)glyoxylic acid,
2-(5-cyclopentylmethyl-2-pyrrolyl)glyoxylic acid,
2-[5-(2-cyclopent-2-enyl)ethyl-2-pyrrolyl]glyoxylic acid and the pharmaceutically acceptable sodium, potassium, calcium, ammonium and amine salts thereof, the corresponding 2-(5-substituted-2-pyrrolyl)glycines and 2-(5-substituted-2-pyrrolyl)glycinamides of formula (II) wherein $R^2$ is hydroxy or amino, their pharmaceutically acceptable acid addition salts and the pharmaceutically acceptable sodium, potassium, ammonium, calcium and the amine salts of said compounds of formula (II) wherein $R^2$ is hydroxy.

The invention further provides a method of treating mammalian subjects, including humans, suffering from a disease or condition attributable to reduced blood flow, reduced oxygen availability or reduced carbohydrate metabolism in the cardiovascular system which comprises orally or parenterally administering to said subject a cardiovascular blood flow, oxygen availability or carbohydrate metabolism increasing amount of a compound of formula (I), (II) or a pharmaceutically acceptable salt thereof.

Also provided are pharmaceutical compositions comprising a pharmaceutically acceptable carrier and a cardiovascular blood flow, oxygen availability or carbohydrate metabolism increasing amount of a compound of formula (I), (II) or a pharmaceutically acceptable salt thereof.

DETAILED DESCRIPTION OF THE INVENTION

The compounds of the formula (I) are obtained from the corresponding 2-substituted-pyrroles of the formula:

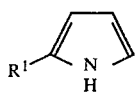

(III)

where $R^1$ is as previously defined, by reacting with an acid chloride of the formula ClCOCOZ where Z is chlorine or an alkoxy group having from one to four carbon atoms, followed, in the case where Z is chlorine, by hydrolysis to give compounds of the formula (I) wherein R is hydrogen, or by reaction with a one to four carbon alkanol to give compounds of the formula (I) where R is alkyl as defined above; and, if desired, hydrolysis of the esters of formula (I), where R is said alkyl group, to yield the corresponding acids where R is hydrogen, and, if desired, forming a salt thereof.

The reaction of the pyrrole of formula (III) with oxalyl chloride is generally performed at a low temperature, e.g., $-70°$ C., in a reaction inert organic solvent, e.g., diethyl ether or methylene chloride, in the presence of an organic base, e.g. pyridine, using a slight molar excess of oxalyl chloride, typically a 10% excess. The reaction is generally complete under these conditions within several hours. The pyrrolylglyoxyloyl chloride intermediate formed need not be isolated but may be reacted directly with the appropriate alcohol to form a compound of formula (I) in which R is alkyl having from one to four carbon atoms. The temperature is allowed to rise somewhat for this step, e.g. to $-20°$ C., and the alcohol, preferably ethanol, is added in excess. Reaction is complete within several minutes and the product is then isolated in a conventional manner, for example by evaporation of the solvent and by recrystallization or chromatography as necessary.

As an alternative process for the preparation of the compounds of the formula (I) the 2-substituted-pyrrole (III) may be reacted with a $C_1$ to $C_4$-alkyl oxalylchloride, (e.g. ethyl oxalylchloride), under similar conditions, to give the esters of formula (I) where R is said alkyl, directly.

The acids of formula (I) wherein R is hydrogen may be prepared by reaction with oxalyl chloride as described above followed by addition of water or, alternatively, by hydrolysis of the esters of formula (I). The hydrolysis reaction may be performed using an alkali-metal base, for example, sodium hydroxide, and is generally performed in a conventional manner, e.g. by warming a mixture of the ester and the aqueous alkali on a steam bath. The hydrolysis is generally complete within several hours. The product may be isolated as the salt, e.g. the sodium salt, or alternatively the solution is neutralized with an acid, e.g. dilute hydrochloric acid and the product isolated as the free acid. When sodium hydroxide is used to perform the hydrolysis, cooling the solution generally results in crystallization of the product as the sodium salt: alternatively the solution is acidified to precipitate the free acid. The product in either case is collected and may be further purified if desired, for example by recrystallization.

Salts with other bases may be prepared by mixing together solutions containing equimolar amounts of the free acid of formula (I) wherein R is hydrogen and the base, e.g. ammonia or arginine. The salt, which generally precipitates from solution is collected by filtration and further purified, if desired, by recrystallization.

Compounds of the formula (II) may be prepared from the corresponding 2-substituted-pyrrole of formula (III) by reaction with glyoxylic acid hydrate in the presence of ammonia to give compounds of the formula (II) wherein $R^2$ is hydroxy. The product may be esterified to give compounds of the formula (II) where $R^2$ is alkoxy as defined above or converted to the amide where $R^2$ is amino or to a pharmaceutically acceptable salt.

The reaction of the 2-substituted pyrrole to give pyrrolyl-amino acids of the formula (II) wherein R is hydroxy is conveniently performed by adding the pyrrole to a stirred solution of glyoxylic acid hydrate (generally using 1 equivalent although a lower amount, e.g. 0.5 equivalents may be employed) in concentrated aqueous ammonium hydroxide. The reaction mixture is maintained at a temperature between room temperature and reflux temperature but we have found that the reaction is conveniently performed at 50°-60° C. and is usually substantially complete within 2-3 hours under these conditions. The product is isolated in a conventional manner, e.g. by washing the reaction mixture with a water immiscible organic solvent, e.g. diethyl ether, to remove unreacted starting material and then acidifying the aqueous solution to the iso-electric point of the amino acid. The product which is generally insoluble is collected by filtration and may be further purified, if desired, by further washing, trituration or recrystallization.

Salts may be prepared from the acid in a conventional manner, e.g. by adding an aqueous solution containing 1 equivalent of a base and evaporation of the resulting solution. Esters may also be prepared from the acid by conventional reactions, but generally it will be found necessary to protect the amino group, with a conventional amino protecting group, e.g. the benzyloxycarbonyl group, before reacting the carboxyl group with, an alkylating reagent, e.g. diazomethane.

The ester is then isolated after removing the protecting group.

The amides of formula (II) where $R^2$ is amino are similarly prepared from the pyrrolylglycines of formula (II) where $R^2$ is hydroxy. In one process according to the invention the amides are prepared from the acid of formula (II) where $R^2$ is hydroxy by first protecting the amino group with a conventional selectively removable amino-blocking group, secondly reacting the carboxyl group with ammonia and finally removing the N-blocking group and, if desired, forming a pharmaceutically acceptable acid addition salt of the product.

Suitable amino-blocking groups and conditions for their introduction and removal are well known to those skilled in the art. One particularly convenient amino-blocking group for use in the process is the benzyloxycarbonyl group. This group is readily introduced by reaction of the amine with benzylchloroformate and is removable by various techniques, the most common being hydrogenation over a palladium catalyst. Thus the pyrrolyl glycine of formula (II) (where $R^2$ is hydroxy) is dissolved in water in the presence of a base, e.g. sodium hydroxide, and benzylchloroformate is added, generally in a slight excess. The reaction may be cooled with advantage and is generally complete within several hours at 0° C.

The product is worked up in a conventional manner, i.e. by neutralization of the solution and solvent extraction. The N-protected product may be further purified, if desired, e.g. by recrystallization, before proceeding to the next stage of the process.

Other protecting groups which may be used include, for example, the t-butyloxycarbonyl, the trityl group, or other protecting groups such as those reviewed by Boissonnas in Advances in Organic Chem. 3, 159–190 (1963).

The reaction of the N-protected amino acid with ammonia is generally performed in the presence of a coupling or activating reagent.

Thus, for example, ammonia may be reacted with the N-protected amino acid in the presence of dicyclohexylcarbodiimide, or an activated ester may be prepared, e.g. the N-hydroxysuccinimide ester. Alternatively, an anhydride or mixed anhydride derivative of the acid may be prepared, e.g. by reaction with isobutylchloroformate. These possibilities and the conditions required for their performance are well known to those skilled in the art. We have found, however, that reaction of the N-hydroxysuccinimido ester is a particularly convenient method.

Thus the N-protected amino acid, dissolved in a reaction-inert organic solvent, e.g. methylene chloride or ethyl acetate, is reacted with a slight excess, e.g. a 10% excess, or N-hydroxysuccinimide in the presence of dicyclohexylcarbodiimide. The reaction is generally complete after the mixture has been allowed to stand at 0° C. for several hours, e.g. overnight, and the solution is filtered to remove the precipitate of dicyclohexylurea and treated directly with ammonia. Formation of the amide proceeds rapidly and is generally complete within several hours at room temperature. The product is isolated in a conventional manner, i.e. by removal of the solvent and solvent extraction and the product may be further purified, if desired, by recrystallization or chromatography.

Finally the N-blocking group is removed. The benzyloxycarbonyl group when present is removed by hydrogenation over a palladium catalyst and this reaction is generally completed within 5–6 hours at room temperature. Other blocking groups are removed using conditions as appropriate for the particular group employed, and the amide of formula (II) where $R^2$ is amino is isolated and purified in a conventional manner as previously described.

In an alternative process the amide of formula (II) where $R^2$ is amino may be prepared directly from the esters of formula (II) where $R^2$ is said alkoxy, particularly the methyl ester, where $R^2$ is a methoxy group, by reacting with ammonia. This reaction is generally achieved by dissolving the compound in concentrated ammonia solution at room temperature for a period of several hours and the amide may then be isolated as previously described.

Salts of the compounds of formula (II) may be prepared from the free amines in a conventional manner, e.g. by adding solutions containing equimolar proportions of the compound of formula (II) and an appropriate pharmaceutically acceptable acid. The product is collected by filtration or by removal of the solvent.

The L-isomers of the pyrrolylglycines, esters and amides of formula (II) may be obtained from the racemic forms by conventional resolution methods. For example, in the case of the acids where $R^2$ is hydroxy, the amino group may be protected with the benzyloxycarbonyl blocking group and a salt formed with an optically active amine, e.g. dihydroabiethylamine or alpha-methyl-benzylamine, followed by fractional crystallization and deprotection by hydrogenolysis. The amides where $R^2$ is amino may be resolved by fractional crystallization of a salt formed with an optically active acid e.g. tartaric acid.

Many of the 2-substituted-pyrroles of formula (III) are known compounds, particularly in the case where $R^1$ is an alkyl group. Their preparation has been described from pyrrole via a Grignard reaction with methyl or ethyl magnesium iodide followed by reaction with an alkylhalide. See, for example, J. Organic Chemistry 32, 228 (1967); J. American Chemical Society 34 43 (1962) and "Rodd's Chemistry of Carbon Compounds," S. Coffey, editor, Elsevier Scientific Publ. Co., New York, Vol. IV, Part A, 1973, pages 337–368.

Other methods have also been employed, e.g. 2-methylpyrrole has been prepared via pyrolysis of 2-formylpyrrolesemicarbazone with potassium hydroxide. Novel alkylpyrroles of formula (II) are generally prepared via a similar Grignard reaction of pyrrole with methyl magnesium iodide followed by reaction with an alkylhalide or alternatively the Grignard reagent is reacted with an acid chloride or ester followed by reduction of the resulting ketone with hydrazine.

The 2-alkylthiopyrroles of formula (III) where $R^1$ is alkylthio or cycloalkylthio are prepared by reaction of pyrrole with thiourea in the presence of iodine and potassium iodide followed by reaction of the resulting thiouronium salt with an alkyl halide or cycloalkylhalide. 2-Alkenyl and substituted alkenylpyrroles may be prepared by reaction of 2-formylpyrrole with the appropriate Wittig reagent.

The compounds of the invention may be administered to patients in admixture with or dissolved in a pharmaceutically acceptable diluent or carrier selected with regard to the intended route of administration and standard pharmaceutical practice.

For example, they may be administered orally in the form of tablets or capsules containing a unit dose of the compound of the formula (I) or (II) together with such excipients as maize starch, calcium carbonate, dicalcium phosphate, alginic acid, lactose, magnesium stearate, talc or certain complex silicates.

The tablets are typically prepared by granulating the ingredients together and compressing the resulting mixture to tablets of the desired size. The capsules are typically prepared by granulating the ingredients together and filling them into hard gelatin capsules of the appropriate size to contain the ingredients.

The compounds may also be administered parenterally, for example by intramuscular, intravenous or subcutaneous injection. For parenteral administration, they are best used in the form of a sterile aqueous solution which may contain other solutes, for example enough salts (e.g. sodium acetate, sodium lactate, sodium citrate, sodium succinate or sodium chloride) or dextrose to make the solution isotonic with blood. A pharmaceutically-acceptable organic solvent such as polyethylene glycol or ethanol may also replace part of the water. An antioxidant such as sodium metabisulphite may also be present, typically in an amount up to 0.1% by weight. Such parenteral formulations may be prepared by conventional methods. For example, in a typical procedure involving the preparation of a succinate-containing intravenous formulation, a 0.2 molar solution of succinic acid may be mixed with a 0.2 molar solution of sodium hydroxide to give a solution of pH 5. The invention compound of the formula I or (II) is then typically dissolved in the succinate solution in an amount of 1–2% on a weight/volume basis. The resulting solution may then be sterilized, for example by filtration, through a bacteria-proof filter under aseptic conditions into sterile containers.

Alternatively, stable parenteral formulations based on isotonic saline solution may be prepared by successively dissolving an antioxidant, e.g. sodium metabisulphite, and sodium chloride in nitrogen-sparged water to give an approximately 0.1 molar sodium chloride solution, dissolving the compound of formula (I) or (II) in solution in an amount of 1–2% on a weight/volume basis and adjusting the pH to about 4 with 0.1 N hydrochloric acid. The solution is then sterilized and filled into containers as already described. Suitable containers are, for example, sterile glass vials of an appropriate size to contain the desired volume of solution, which volume will typically contain one or more unit doses of the compound of the formula (I) or (II). The compounds of the invention may also be administered by the infusion of a parenteral formulation as described above into a vein.

For oral administration to human patients, it is expected that the daily dosage level of a compound of the formula (I) or the L-form of a compound of the formula (II) will be from 5 to 70, preferably 20–50 mg./kg., per day for a typical adult patient (70 kg.). For parenteral administration, it is expected that the daily dosage level of such a compound will be from 1–10, preferably 2–5 mg./kg. per day, for a typical adult patient. Thus tablets or capsules can generally be expected to contain from 150 mg. to 1 g. of the active compound for administration orally up to 5 times a day. Dosage units for parenteral administration can be expected to contain from 70–700 mg. of the active compound. A typical vial could be a 50 ml. vial containing 70–700 mg. of the active compound in 30–50 ml. of solution. The racemic (DL) form of a compound of formula (II) will of course have to be used at approximately twice the levels used for the L-form of the same compound.

It should of course be appreciated that, in any event the physician will determine the actual dosage which will be most suitable for the individual and it will vary with the age, weight and response of the particular patient and the route of administration. The above dosages are exemplary of the average patient, there may of course be individual cases where higher or lower dosage ranges are merited.

The utility of the compounds of the formula (I) or (II) in treating diseases characterized by reduced blood flow, reduced oxygen availability or reduced carbohydrate metabolism in the cardiovascular system, is assessed by virtue of their abilities to:

(1) increase the oxidation of glucose and/or pyruvate by isolated rat muscle preparations in vitro;

(2) increase the proportion of the active form of the enzyme pyruvate dehydrogenase (PDH) in organs of animals (e.g. rats) in vovo; and (3) reduce oxygen demand and affect the relative utilization of carbohydrate and lipid metabolites by the electrically-paced heart of an anesthetized dog in the presence or absence of an isoprenaline stimulus.

Activity in these tests is indicative of the potential utility of the compounds in the treatment of ischaemic heart disease and cardiac failure.

The compounds of the formula (I) and (II) have been tested for their ability to increase the oxidation of glucose and/or pyruvate as follows:

Diaphragm tissue is obtained from rats fed on a high fat diet similar to 'Diet B' described by Zaragoza and Felber [*Horm, Metab. Res.*, 2, 323 (1970)]. Pyruvate oxidation by such tissue is assessed by measurement of the rate of incorporation of carbon-14 from carbon-14-labelled pyruvate into carbon dioxide in vitro, as described by Bringolf [*Eur. J. Biochem.*, 26, 360 (1972)]. The rate of pyruvate oxidation is depressed by 50–75% compared with that by diaphragm tissue from rats fed on a normal diet. When the compounds of the invention are added to the medium, they are found to stimulate pyruvate oxidation by diaphragm tissue from fat-fed rats in a dose dependent manner.

The degree of stimulation at a concentration of 0.5 mmolar by various of the compounds of the Examples is shown in the following Table:

| Example | % Stimulation | Example | % Stimulation |
|---------|---------------|---------|---------------|
| 1       | 32            | 31      | 125           |
| 2       | 50            | 32      | 43            |
| 9       | 65            | 33      | 69            |

-continued

| Example | % Stimulation | Example | % Stimulation |
|---------|---------------|---------|---------------|
| 18 | 19 | 34 | 53 |
| 20 | 66 | 35 | 209 |
| 21 | 147 | 36 | 154 |
| 22 | 51 | 37 | 124 |
| 23 | 78 | 38 | 80 |
| 24 | 140 | 39 | 44 |
| 25 | 59 | 40 | 80 |
| 26 | 31 | 59 | 29 |
| 27 | 157 | 60 | 59 |
| 28 | 88 | 61 | 84 |
| 29 | 78 | 64 | 87 |
| 30 | 44 | | |

The rate of glucose oxidation by isolated hearts from starved rats is measured in a recirculating oxygenated perfusion system, by measuring the rate of incorporation of carbon-14 from carbon-14-labelled glucose into carbon dioxide using a method similar to those described by Morgan et al. [*J. Biol. Chem.*, 236, 253 (1961)] and by Randle et al. [*Biochem. J.*, 93, 652 (1964)].

The ability of the compounds of this invention to increase the proportion of the active form of the pyruvate dehydrogenase enzyme has been measured in the following test:

Rats fed on a high fat diet as in the previous test, are treated either with placebo or with the compound of formula (I) or (II) by subcutaneous or intravenous injection or by oral administration. After 1.5 hours the rat hearts are removed and homogenized under conditions which minimize changes in the proportion of the pyruvate dehydrogenase enzyme (PDH) which is present in the active form, as described by Whitehouse and Randle [*Biochem. J.*, 134, 651 (1973)]. The total amount of enzyme present (PDHt) and the amount which is present in the active form (PDHa) are assessed by a method similar to that described by Taylor et al. [*J. Biol. Chem.*, 248, 73 (1973)]. The fat-feeding process is found to depress the ratio PDHa/PDHt from a normal value of about 0.7 to a value in the range from 0.05 to 0.2. Treatment of fat-fed rats with the compounds of formula (I) or (II) either parenterally or orally, increases this ratio in a dose dependent manner.

The increase in the PDHa/PDHt ratio affected by various of the compounds for the Examples at the dose level indicated is shown in the following Table: The compounds were administered by subcutaneous injection except where indicated by (0) where the compounds were administered orally.

| | | PDHa/PDHt ratio | | |
|---------|---------|-----------------|---------------|---------------|
| Example | Placebo | 1.2 mMol/kg. | 0.6 mMol/kg. | 0.3 mMol/kg. |
| 6 | 0.13 | | | 0.23 (0) |
| 20 | 0.18 | 0.85 | | |
| 21 | 0.14 | | 0.71 | 0.44 |
| 22 | 0.14 | 0.84 | | |
| 23 | 0.17 | 0.82 | 0.66 | |
| 24 | 0.25 | | | 0.42 |
| 25 | 0.20 | 1.00 | 0.45 | |
| 27 | 0.14 | | 0.13 | |
| 29 | 0.13 | | | 0.40 (0) |
| 31 | 0.08 | | | 0.20 (0) |
| 32 | 0.20 | 0.83 | 0.16 | |
| 33 | 0.14 | | | 0.13 |
| 34 | 0.11 | 0.42 | | |
| 35 | 0.14 | | | 0.18 |
| 36 | 0.13 | | | 0.20 |
| 37 | 0.17 | | | 0.12 |
| 38 | 0.17 | | | 0.25 |
| 40 | 0.23 | | | 0.27 |

-continued

| | | PDHa/PDHt ratio | | |
|---------|---------|-----------------|---------------|---------------|
| Example | Placebo | 1.2 mMol/kg. | 0.6 mMol/kg. | 0.3 mMol/kg. |
| 59 | 0.13 | | 0.21 (0) | |
| 60 | 0.08 | | 0.16 | |
| 61 | 0.09 | | 0.13 (0) | |
| 64 | 0.13 | | 0.27 | |

The ability of compounds of formula (I) or (II) to reduce oxygen demand and affect the relative utilization of carbohydrate and lipid metabolites in the heart has been assessed by measuring the effect of the compounds on myocardial blood flow and metabolism in fasted, closed-chest, anaesthetized beagle dogs, with cardiac catherization to enable simultaneous sampling of coronary sinus and arterial blood to be carried out. Coronary sinus blood flow is measured by the hydrogen gas clearance technique described by Aukland et al. [*Circulation Res.*, 14, 164 (1964)]. The heart is paced electrically at 155 beats/minute and recordings of hemodynamic parameters (blood pressure, left ventricular pressure and the first derivative of the latter) are made continuously. Control measurement of coronary blood flow are made and samples of blood taken at 40 minute intervals, both in an untreated animal and in the same animal dose with an infusion of isoprenaline (60 ng./kg./min.), which both stimulates cardiac contraction and increases plasma free fatty acid levels. The compound of formula (I) or (II) is then administered intravenously and measurements are made and samples taken again, 40 minutes and 90 minutes later. The blood samples from the artery and coronary sinus are analyzed for oxyhemoglobin, pyruvate and free fatty acid (FFA) content, differences between those of the arterial and coronary sinus blood, when multiplied by coronary blood flow, being a measure of oxygen consumption, pyruvate uptake and FFA uptake by the myocardium respectively.

It is found that DL-2-(5-cyclopropylmethyl-2-pyrrolyl)glycinamide at doses of 0.02 to 0.1 millimole/kg. increases myocardial pyruvate uptake by at least 2-fold, both in the presence and absence of isoprenaline, for a period of at least 40 minutes after dosing, in keeping with its proven action as a PDH stimulator. Myocardial oxygen consumption is descreased by about 20% in the presence of isoprenaline.

Myocardial FFA uptake is decreased by about 50% in the presence of isoprenaline while myocardial glucose uptake was increased. There is no significant affect on myocardial blood flow or any of the hemodynamic parameters measured.

The preparation of the novel compounds of the invention is described in the following Examples. Preparations 1 to 7 are provided to illustrate preparation of the 2-alkylpyrrole starting materials of formula (III). Temperatures are given in ° Centigrade.

EXAMPLE 1

5-Methyl-2-pyrrolylglyoxylic Acid Ethyl Ester

Pyridine (8.80 g.) in dry methylene chloride (100 ml.) was added dropwise to a stirred solution of oxalyl chloride (13.96 g.) in dry methylene chloride (300 ml.) at −70° to give a white precipitate. The mixture was stirred at −70° for 15 minutes and then a solution of 2-methylpyrrole (8.10 g.) in dry methylene chloride (75 ml.) was added over 30 minutes. The mixture was stirred at −70° for a further 3 hours and then allowed to warm up to −20° giving a clear solution. Ethanol (25 ml.) was added and the solution was allowed to reach room temperature. The solution was washed with N hydrochloric acid (3×100 ml.) followed by water (3×100 ml.) and then dried over sodium sulphate. Evaporation of the solvent gave a dark oil which solidified on standing. The solid was dissolved in hot petroleum ether (B.P. 60°–80°) and some insoluble material was filtered off. The solid which crystallized from the cooled filtrate was chromatographed on silica gel. Elution with a mixture of chloroform and petroleum ether (B.P. 60°–80°) (3:1) gave a solid which was crystallized from petroleum ether (B.P. 60°–80°) to give 5-methyl-2-pyrrolylglyoxylic acid ethyl ester (11.4 g.), M.P. 72°–74°. Found: C, 59.72; H, 6.54; N, 7.47. $C_9H_{11}NO_3$ requires: C, 59.66; H, 6.16; N, 7.77%.

Other pyrrolylglyoxylic esters prepared similarly are listed in the table below.

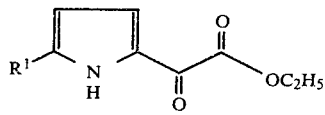

| Example | $R^1$ | M.P. °C. | Analysis, percent (Theoretical Figures in Brackets) | | |
|---|---|---|---|---|---|
| | | | C | H | N |
| 2 | $C(CH_3)_3$ | 93–94 | 64.58 (64.55 | 7.76 7.68 | 6.29 6.27) |
| 3 | $C_2H_5$ | (not purified) | | | |
| 4 | $SCH_3$ | 49–50 | 50.84 (50.69 | 5.13 5.20 | 6.76 6.57) |

EXAMPLE 5

5-n-Propyl-2-pyrrolylglyoxylic Acid Ethyl Ester

Pyridine (3.50 g., 0.044 mole) in dry methylene chloride was added dropwise to a stirred solution of ethyl oxalyl chloride (5.75 g., 0.042 mole) in dry methylene chloride (50 ml.) at −70° and the resulting mixture was stirred at −70° for 15 minutes. A solution of 2-n-propylpyrrole (4.36 g., 0.040 mole) in dry methylene chloride (50 ml.) was then added over 15 minutes. The mixture was stirred at −70° for 3 hours and then allowed to warm up to room temperature. The mixture was washed with 100 ml. N hydrochloric acid followed by water (2×100 ml.) and dried over $Na_2SO_4$. Evaporation of the solvent gave an oil which solidified on standing. The solid was crystallized from petroleum ether (B.P. 40°–60°) to give 5-propyl-2-pyrrolylglyoxylic acid ethyl ester (7.30 g.) M.P. 48°–49°. Found C, 62.98; H, 7.27; N, 6.80. $C_{11}H_{15}NO_3$ requires: C, 63.14; H, 7.23; N, 6.69%.

EXAMPLES 6–19

Other pyrrolylglyoxylic esters prepared similarly from the appropriate alkylpyrrole are listed in the table below.

| Example | $R^1$ | M.P. °C. | Analysis, percent (Theoretical Figures in Brackets) | | |
|---|---|---|---|---|---|
| | | | C | H | N |
| 6 | $n-C_4H_9$ | 55–56 | 64.55 (64.55 | 7.71 7.68 | 6.20 6.27) |
| 7 | $n-C_5H_{11}$ | 40–42 | 65.80 (65.82 | 8.07 8.15 | 5.90 5.97) |
| 8 | $n-C_6H_{13}$ | 50–52 | 67.10 (66.90 | 8.55 8.42 | 5.54 5.57) |
| 9 | $CH_2CH(CH_3)_2$ | 61–62 | 64.91 (64.55 | 7.87 7.68 | 6.33 6.27) |
| 10 | $CH_2C(CH_3)_3$ | 96–97 | 65.89 (65.80 | 8.11 8.07 | 6.04 5.90) |
| 11 | $CH_2CH_2C(CH_3)_3$ | 52–53 | 67.32 (66.90 | 8.68 8.42 | 5.71 5.57) |
| 12 | $CH_2$–cyclopropyl | 61–62 | 65.39 (65.41 | 6.91 6.83 | 6.60 6.33) |
| 13 | $CH_2$–cyclobutyl | 57–59 | 67.47 (67.44 | 7.71 7.68 | 5.81 5.62) |
| 14 | $CH_2$–cyclohexyl | 87–88 | 68.07 (68.41 | 8.04 8.04 | 5.45 5.32) |
| 15 | $CH_2CH_2$–cyclopentyl | 63–64 | 68.15 (68.41 | 8.14 8.04 | 5.30 5.32) |
| 16 | $CH_2CH_2$–cyclopentenyl | 62–63 | 68.83 (68.94 | 7.38 7.33 | 5.36 5.36) |
| 17 | $CH_2CH_2$–cyclohexyl | 73–74 | 68.96 (69.28 | 8.46 8.35 | 5.23 5.05) |
| 18 | $CH_2$–phenyl | 79–80 | 70.51 (70.02 | 5.94 5.88 | 5.47 5.44) |
| 19 | $CH_2CH_2$–phenyl | 72–73 | 70.61 (70.83 | 6.19 6.32 | 5.34 5.16) |

EXAMPLE 20

5-Ethyl-2-Pyrrolylglyoxylic Acid

A mixture of 5-ethyl-2-pyrrolylglyoxylic acid ethyl ester (1.95 g.) and sodium hydroxide (0.44 g.) in water (25 ml.) was heated on a steam bath for 1.5 hours. The mixture was cooled, filtered and the filtrate was acidified with 2 N hydrochloric acid. The solid was filtered off, washed with a little water, dried and crystallized from toluene to give 5-ethyl-2-pyrrolylglyoxylic acid (1.40 g.), M.P. 126°–128°). Found: C, 57.55; H, 5.53; N, 8.70. $C_8H_9NO_3$ requires: C, 57.48; H, 5.43; N, 8.38%.

EXAMPLE 21

5-Cyclopropylmethyl-2-pyrrolylglyoxylic Acid Sodium Salt

A mixture of 5-cyclopropylmethyl-2-pyrrolylglyoxylic acid ethyl ester (6.63 g.) and sodium hydroxide (1.32 g.) was heated in water (40 ml.) as described in Example 20. The resulting solution was cooled to 5° and the solid was filtered off and crystallized from acetone to give 5-cyclopropylmethyl-2-pyrrolylglyoxylic acid sodium salt hydrate (3.3 g.), M.P. 228°–232°. Found: C, 51.50; H, 5.19; N, 5.91. $C_{10}H_{10}NO_3Na \cdot H_2O$ requires: C, 51.50; H, 5.19; N, 6.01%.

When equivalent amounts of potassium hydroxide or calcium hydroxide are used in place of sodium hydroxide, the corresponding potassium or calcium salt is obtained.

EXAMPLES 22-38

The following glyoxylic acids were prepared from the corresponding ester and isolated either as the free acids (Examples 22-34) as described in Example 20 or as the sodium salts (Examples 35-38) as described in Example 21.

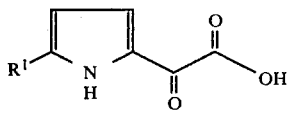

| Example | R¹ | M.P. °C. | Analysis, percent (Theoretical Figures in Brackets) | | |
|---|---|---|---|---|---|
| | | | C | H | N |
| 22 | CH₃ | 163-165 | 54.56 (54.90) | 4.62 4.61 | 9.10 9.15) |
| 23 | n-C₃H₇ | 89-90* | 59.53 (59.66) | 6.22 6.12 | 7.77 7.73) |
| 24 | n-C₄H₉ | 89-90 | 61.49 61.52 | 6.73 6.71 | 7.21 7.18) |
| 25 | CH₂CH(CH₃)₂ | 104-105 | 61.19 (61.52) | 6.66 6.71 | 6.84 7.18) |
| 26 | t-C₄H₉ | 128-129 | 61.68 (61.52) | 6.72 6.71 | 7.19 7.18) |
| 27 | n-C₅H₁₁ | 94-95 | 63.45 (63.14) | 7.13 7.23 | 6.72 6.69) |
| 28 | CH₂C(CH₃)₃ | 138-139 | 63.40 (63.14) | 7.28 7.23 | 6.81 6.69) |
| 29 | n-C₆H₁₃ | 89-90 | 64.60 (64.55) | 7.67 7.67 | 6.64 6.27) |
| 30 | CH₂CH₂C(CH₃)₃ | 141-142 | 64.44 (64.55) | 7.66 7.67 | 6.36 6.27) |
| 31 | CH₂CH₂-cyclohexyl | 135-137 | 67.45 (67.57) | 7.68 7.83 | 5.62 5.79) |
| 32 | CH₂-phenyl | 148-149 | 67.68 (68.11) | 4.82 4.84 | 6.08 6.11) |
| 33 | CH₂CH₂-phenyl | 252-253 | 63.46 (63.39) | 4.53 4.56 | 5.03 5.28) |
| 34 | SCH₃ | 164-165 | 46.28 (45.40) | 4.02 3.81 | 7.78 7.56) |
| 35 | CH₂CH₂-cyclobutyl | 198 (d) | 60.98 (61.17) | 5.53 5.53 | 5.45 5.49) |
| 36 | CH₂-cyclopropyl | 266-269 | 58.87 (59.25) | 5.79 5.89 | 5.87 5.76) |
| 37 | CH₂-cyclohexyl | >270 | 60.78 (60.69) | 6.37 6.27 | 5.61 5.45) |
| 38 | CH₂CH₂-cyclopropyl | 240 (d) | 60.64 (60.69) | 6.19 6.27 | 5.15 5.45) |

*Also obtained in another crystalline form m.p, 67-68°.

EXAMPLE 39

5-n-Propylthio-2-pyrrolylglyoxylic Acid Ethyl Ester (A) A mixture of pyrrole (6.7 g., 0.10 mole) and thiourea (7.6 g., 0.10 mole) in 50% aqueous ethanol (500 ml.) was stirred at room temperature under nitrogen while a solution of potassium iodide (16.6 g., 0.10 mole) and iodine (12.7 g., 0.05 mole) in water (100 ml.) was added dropwise. The solution was cooled to 0° and a solution of propyl iodide (18 g., 0.105 mole) in methanol (20 ml.) was added followed by the dropwise addition of a solution of potassium hydroxide (5.6 g.) in 50% aqueous methanol (40 ml.). The mixture was stirred for a further 1.5 hours at room temperature and the solution then neutralized by the addition of solid carbon dioxide. The reaction mixture was poured into a solution of sodium chloride (25 g.) in water (100 ml.) and the solution extracted with methylene chloride (3×50 ml.). The organic extracts were combined, dried over sodium sulphate and the solvent evaporated to give an oil which was distilled under reduced pressure to yield 2-n-propylthiopyrrole (1.0 g.), B.P. 115° at 15 mm.

(B) Pyridine (7.9 g.) on dry methylene chloride (75 ml.) was added dropwise to a stirred solution of ethyl oxalyl chloride (8.60 g., 0.063 mole) in dry dichloromethane (75 ml.) at −30° and, after 15 minutes, a solution of 2-n-propylthiopyrrole (8.5 g., 0.06 mole) in methylene chloride (100 ml.) was added dropwise. The solution was stirred at −30° for 3 hours and then allowed to warm to −10° and 0.05 N hydroxhloric acid (250 ml.) added. The organic layer was diluted with chloroform (100 ml.) and separated and the aqueous phase extracted with chloroform.

The combined organic extracts were washed with saturated brine (50 ml.), dried over MgSO₄ and evaporated. The resulting oil was distilled at 0.1 mm, and the fraction boiling between 165°-175° collected and recrystallized from hexane at −70° to give 5-n-propylthio-2-pyrrolyl-glyoxylic acid ethyl ester as a yellow solid (3.5 g.). The product was further purified by chromatography on silica, M.P. 34°. Found: C, 54.29; H, 6.08; N, 6.05. C₁₁H₁₅NO₃S requires: C, 54.75; H, 6.27; N, 5.18%.

EXAMPLE 40

5-n-Propylthio-2-pyrrolylglyoxylic Acid

A mixture of 5-n-propylthio-2-pyrrolylglyoxylic acid ethyl ester (2.4 g.) and sodium hydroxide (1.0 g.) in water (100 ml.) was heated on a steam bath for 3 hours. The solution was cooled, acidified to pH 1 with dilute hydrochloric acid and the product extracted with chloroform. Evaporation of the solvent and recrystallization from petroleum ether (B.P. 40°-60°) gave 5-n-propylthio-2-pyrrolylglyoxylic acid (0.7 g.) as yellow crystals, M.P. 87°. Found: C, 50.34; H, 5.21; N, 6.54. C₉H₁₁NO₃S requires: C, 50.68; H, 5.20; N, 6.57%.

EXAMPLES 41-44

The procedures of Examples 39 and 40 were followed but starting with the appropriate bromide or iodide to give the following compounds:

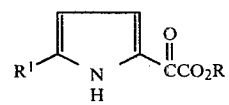

| Example | R¹ | R | M.P. °C. | Analysis, percent (Theoretical Figures in Brackets) | | |
|---|---|---|---|---|---|---|
| | | | | C | H | N |
| 41 | CH₃CH₂S | CH₂CH₃ | 38-39 | — | — | — |
| 42 | CH₃CH₂S | H | 97 | 48.13 (48.23) | 4.45 4.55 | 7.05 7.03) | yellow solid, M.P. 46°. Found: C, 56.81; H, 6.23; N, 5.38. $C_{12}H_{15}NO_3S$ requires: C, 56.89; H, 5.97; N, 5.53%.

EXAMPLES 46-51

The following compounds were prepared by the general procedure of Example 5 but starting with the appropriate 2-substituted-pyrrole.

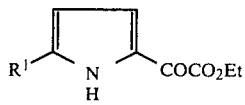

| Example | R¹ | M.P. °C. | C | H | N |
|---|---|---|---|---|---|
| 46 | Cl—⟨⟩—CH=CH— trans | 175–177 | 62.82 (63.27 | 4.58 4.65 | 5.01 4.01) |
| 47 | Cl—⟨⟩—CH=CH— cis | 138–140 | 63.09 (63.27 | 4.58 4.65 | 4.38 4.61) |
| 48 | (CH₃)₃C—⟨⟩—CH=CH— trans | 163–165 | 73.73 (73.82 | 7.06 7.12 | 4.10 4.30) |
| 49 | ▷—CH=CH— cis/trans | 64–65 | 66.19 (66.93 | 6.61 6.48 | 5.98 6.01) |
| 50 | CH₃CH=CH | 68–73 | 63.32 (63.75 | 6.30 6.32 | 7.11 6.76) |
| 51 | ▷—CH₂—CH₂— | 56–58 | 66.12 (66.36 | 7.32 7.28 | 6.11 5.95) |

EXAMPLES 52-56

Hydrolysis of the esters of Examples 46 to 51 with sodium hydroxide as previously described yielded the following 2-pyrrolylglyoxylic acids:

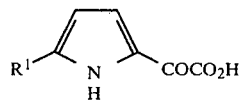

| Example | R¹ | M.P. °C. | C | H | N |
|---|---|---|---|---|---|
| 52 | Cl—⟨⟩—CH=CH— Trans | 245 (dec.) | 61.07 (60.99 | 4.06 3.66 | 4.89 5.08) |
| 53 | Cl—⟨⟩—CH=CH— Cis | >250 | 56.94 (56.48 | 3.17 3.0 | 4.85 4.71)* |
| 54 | (CH₃)₃C—⟨⟩—CH=CH— Trans | 215–219 | 72.92 (72.70 | 6.41 6.44 | 4.76 4.71) |
| 55 | ▷—CH=CH— Trans | 179–180 | 63.29 (64.38 | 5.41 5.40 | 6.55 6.83) |
| 56 | CH₃—CH=CH— | 119–120 | 60.04 | 5.05 | 7.38 |

-continued

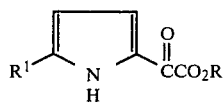

| Example | R¹ | R | M.P. °C. | C | H | N |
|---|---|---|---|---|---|---|
| 43 | ⟨⟩—CH₂S | CH₂CH₃ | 66 | 62.44 (62.26 | 5.31 5.23 | 4.82 4.84) |
| 44 | ⟨⟩—CH₂S | H | 118 | 60.27 (59.75 | 4.34 4.24 | 5.55 5.36) |

EXAMPLE 45

5-Cyclopropylmethylthio-2-pyrrolylglyoxylic Acid Ethyl Ester (A) A solution of 2-thiocyanopyrrole (12.4 g., 0.1 mole) and cyclopropylmethyl bromide (14.85 g., 0.11 mole) in methanol (500 ml.) was cooled below 0° (ice-salt bath), and stirred vigorously under nitrogen while a solution of potassium hydroxide (12.3 g., 0.22 mole) in 1:1 (by volume) aqueous methanol (400 ml.) was added dropwise during 0.75 hours. The cooling bath was removed and stirring continued for 1.5 hours before neutralization of the excess alkali with solid carbon dioxide. The reaction mixture was poured into 20% brine (500 ml.) and extracted with methylene chloride (3×100 ml.). The combined organic extracts were dried ($Na_2SO_4+K_2CO_3$), then evaporated in vacuo to provide a red oil (12.1 g.). Distillation of this crude oil afforded 2-cyclopropylmethylthio-pyrrole as a colorless oil (5.8 g. 38%), B.P. 138°–141° at 11 mm. (B) The product from Part A was reacted with ethyl oxalyl chloride as described in Example 39, Part B. Chromatography on silica followed by recrystallization from petroleum ether (B.P. 40°–60°) and hexane gave 5-cyclopropylmethylthio-2-pyrrolylglyoxylic acid ethyl ester as a -continued

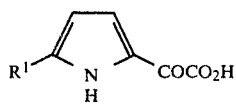

| Example | R¹ | M.P. °C. | Analysis, Percent (Theoretical in Brackets) | | |
|---|---|---|---|---|---|
| | | | C | H | N |
| | | | (60.33 | 5.06 | 7.82) |

*Sodium salt

EXAMPLE 57

When the appropriate 5-substituted pyrrole of formula (III) and alkyl oxalyl chloride are employed as starting materials in the procedure of Example 5 the following compounds are obtained.

$$R^1 \underset{\underset{H}{N}}{\diagdown} COCOOR$$

| R¹ | R | R¹ | R |
|---|---|---|---|
| n-C₁₀H₂₁ | CH₃ | 3-ClC₆H₄(CH₂)₄ | CH₃ |
| n-C₈H₁₇ | n-C₃H₇ | 4-CH₃C₆H₄CH₂ | C₂H₅ |
| (CH₃)₂CH(CH₂)₇ | n-C₄H₉ | cyclohexenyl-CH=CHCH₂ | n-C₃H₇ |
| CH=CHCH₂ | i-C₃H₇ | cyclohexenyl-CH(CH₃)CH₂ | n-C₄H₉ |
| CH₃CH=CHCH₂ | sec-C₄H₉ | 3-FC₆H₄CH=CHCH₂ | i-C₄H₉ |
| (CH₃)₂CH=CHCH₂ | t-C₄H₉ | 4-CH₃OC₆H₄CH₂CH=CHCH₂ | CH₃ |
| CH₃CH=CH(CH₂)₃ | CH₃ | cycloheptenyl-CH=CHCH₂ | C₂H₅ |
| CH₃CH=CH | n-C₄H₉ | cyclohexenyl-CH₂CH=CHCH₂ | C₂H₅ |
| C₂H₅ | C₂H₅ | cyclohexenyl-CH=C(CH₃)CH₂ | i-C₃H₇ |
| cyclohexyl-(CH₂)₃ | CH₃ | C₆H₅CH₂CH₂ | n-C₃H₇ |
| cyclohexyl-(CH₂)₄ | n-C₃H₇ | 4-BrC₆H₄CH(CH₃)CH₂ | CH₃ |
| cycloheptyl-CH₂ | n-C₄H₉ | 4-IC₆H₄CH₂CH₂ | n-C₄H₉ |
| cyclopropyl-(CH₂)₄ | i-C₄H₉ | 4-n-C₄H₉OC₆H₄CH₂ | C₂H₅ |
| cyclopentenyl-CH₂CH=CHCH₂ | CH₃ | cyclohexyl-CH=CH | i-C₃H₇ |
| cyclopentenyl-CH₂CH₂ | | | |

-continued

| | |
|---|---|
| | R¹⟨pyrrole-NH⟩COCOOR |
| | CH₃ |
| ⟨cyclohexenyl⟩-CH₂CH₂ | |
| ⟨cyclohexenyl⟩-CH₂ | C₂H₅ |

| R | R |
|---|---|
| 2-FC₆H₄CH₂ | C₂H₅ |
| | C₂H₅ |
| ⟨cyclopentyl⟩-C(CH₃)=CH | |
| ⟨cycloheptenyl⟩-CH=CH | n-C₃H₇ |
| ⟨cyclohexyl⟩-(CH₂)₂CH=CH | CH₃ |
| | C₂H₅ |
| ⟨cyclopentenyl⟩-CH=CH | |
| C₆H₅CH(CH₃)CH=CH | CH₃ |
| 4-IC₆H₄CH=CH | n-C₄H₉ |
| 4-CH₃OC₆H₄CH=CH | i-C₄H₉ |
| 4-n-C₄H₉OC₆H₄C(CH₃)=CH | n-C₄H₉ |
| 3-CH₃C₆H₄(CH₂)₂CH=CH | CH₃ |
| 4-n-C₄H₉C₆H₄CH=CH | C₂H₅ |
| ⟨cyclohexenyl⟩-(CH₂)₂CH=CH | i-C₃H₇ |
| ⟨cycloheptenyl⟩-CH=CH | t-C₄H₉ |

Hydrolysis of the above esters by the procedures of Examples 20 and 21 provides the corresponding carboxylic acids and sodium salts, respectively.

EXAMPLE 58

By employing the appropriate starting materials in the procedures of Examples 39 and 45 the following thiopyrrole compounds are prepared.

R¹⟨pyrrole-NH⟩COCOOR

| R¹ | R | R¹ | R |
|---|---|---|---|
| CH₃S | CH₃ | ⟨cyclohexenyl⟩-CH₂CH(CH₃)CH₂S | CH₃ |
| n-C₄H₉S | C₂H₅ | 4-ClC₆H₄CH₂CH₂S | C₂H₅ |
| (CH₃)₂CHCH₂S | n-C₄H₉ | 3-BrC₆H₄(CH₂)₃S | n-C₃H₇ |
| n-C₁₀H₂₁S | i-C₃H₇ | 2-IC₆H₄(CH₂)₄S | n-C₄H₉ |
| ⟨cyclopentyl⟩-S | CH₃ | 3-C₂H₅C₆H₄CH₂CH₂S | CH₃ |

-continued

| R¹ | R | R¹ | R |
|---|---|---|---|
| 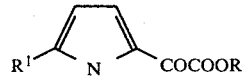—S | sec-C₄H₉ | 4-t-C₄H₉C₆H₄(CH₂)₃S | CH₃ |
| —S | t-C₄H₉ | 2-CH₃OC₆H₄(CH₂)₃S | C₂H₅ |
| —CHCH₂S | CH₃ | 4-t-C₄H₉OC₆H₄CH₂S | C₂H₅ |
| 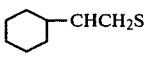—(CH₂)₄S | C₂H₅ | | |
| 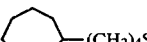—CH₂CH₂S | n-C₃H₇ | | |
| 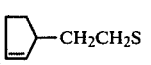—CH₂S | C₂H₅ | | |
| 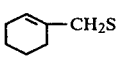—CH₂S | C₂H₅ | | |
| —(CH₂)₄S | C₂H₅ | | |

EXAMPLE 59

DL-2-(5-Cyclopropylmethyl-2-pyrrolyl)glycine

Glyoxylic acid hydrate (8.3 g., 0.09 mole) was dissolved in 0.880 sp. gr. ammonia solution (50 ml.) and the solution heated to 50°–60°. 2-Cyclopropylmethyl pyrrole (10.9 g., 0.09 mole) was added dropwise and the resulting mixture stirred at 50°–60° for 2 hours. Diethyl ether (50 ml.) was added to the cool reaction mixture. Filtration gave a solid which was washed with diethyl ether (50 ml.). The filtrate was shaken and the aqueous phase separated and combined with the filtered solid to give a slurry whose pH was adjusted to ca. 5 with concentrated hydrochloric acid. The mixture was filtered and the resulting solid thoroughly washed with water, acetone, and with diethyl ether, affording, after drying in vacuo, DL-2-(5-cyclopropylmethyl-2-pyrrolyl)glycine (9.65 g., 55%), M.P. 203°–205° (decomp.).

Found: C, 61.51; H, 7.24; N, 14.51. C₁₀H₁₄N₂O₂ requires: C, 61.84; H, 7.26; N, 14.42%.

EXAMPLE 60

DL-2-(5-Ethyl-2-pyrrolyl)glycine

2-Ethylpyrrole (4.75 g., 0.05 mole) was added dropwise to a stirred solution of glyoxylic acid hydrate (2.3 g., 0.025 mole) in 0.880 sp. gr. ammonia solution (25 ml.) at 50°. The mixture was stirred at 50° for 4 hours, then cooled, acidified to pH 5.5 with concentrated hydrochloric acid and filtered. The resulting solid was washed with water, triturated with cold, then hot; methanol and dried in vacuo to afford DL-2-(5-ethyl-2-pyrrolyl)glycine (1.8 g., 43%), M.P. 188° (decomp.).

Found: C, 57.08; H, 7.10; N, 16.64. C₈H₁₂N₂O₂ requires: C, 57.12; H, 7.19; N, 16.66%.

EXAMPLE 61

DL-2-(5-n-Pentyl-2-pyrrolyl)glycine was prepared as described in Example 60 above but using 2-n-pentylpyrrole (6.85 g., 0.05 mole) to give, DL-2-(5-n-pentyl-2-pyrrolyl)glycine (1.6 g., 30%), M.P. 190°–195°. (decomp.).

Found: C, 62.75; H, 8.47; N, 13.85. C₁₁H₁₈N₂O₂ requires: C, 62.83; H, 8.63; N, 13.32%.

EXAMPLE 62

DL-2-[5-(2-cyclopropylvinyl)-2-pyrrolyl]glycine cis-/trans-2-(2-Cyclopropylvinyl)pyrrole (3.0 g., 0.023 mole) was added to a stirred solution of glyoxylic acid hydrate (2.1 g., 0.023 mole) in 0.880 (sp. gr.) ammonia solution (15 ml.) and the reaction mixture heated at 60° for 2.5 hours, then allowed to cool. The pH was adjusted to 5–6 with concentrated hydrochloric acid, and the mixture was then filtered. The resulting solid was washed with water, acetone and diethyl ether, and dried under vacuum to provide DL-2-[5-(2-cyclopropylvinyl)-2-pyrrolyl]glycine as a pink solid (1.2 g.), M.P. 275°.

Found: C, 63.56; H, 6.96; N, 13.57. C₁₁H₁₄N₂O₂ requires: C, 64.06; H, 6.84; N, 13.58%.

The ratio of cis-trans-isomers was indeterminable by ¹H N.M.R. spectroscopy.

EXAMPLE 63

DL-2-[5-(2-Cyclopropylethyl)-2-pyrrolyl]glycine

This compound was prepared as described for Example 62 but starting with 2-(2-cyclopropylethyl)pyrrole (2.0 g., 0.015 mole) to give the required DL-2-[5-(2-cyclopropylethyl)-2-pyrrolyl]glycine as a pale pink solid (0.70 g.), M.P. 198°–200° (decomp.).

Found: C, 63.57; H, 7.92; N, 13.22. C₁₁H₁₆N₂O₂ requires: C, 63.44; H, 7.74; N, 13.45%.

EXAMPLE 64

DL-2-(5-Cyclopropylmethyl-2-pyrrolyl)glycinamide

A. DL-2-(5-Cyclopropylmethyl-2-pyrrolyl)glycine (20 g.) was added to a warm aqueous solution of sodium hydroxide (32 g.) and stirred to give a clear solution. Ice (200 g.) was added followed by benzylchloroformate (25 g.). The reaction mixture was stirred rapidly at 0° for 2.2 hours and then acidified to pH 4 with concentrated hydrochloric acid.

The precipitate of unreacted starting material was removed by filtration and washed with ethyl acetate. The aqueous filtrate was extracted several times with ethyl acetate and the combined organic washings and extracts were dried over magnesium sulphate and evaporated to dryness. The solid residue was triturated with dry diethyl ether, filtered off and washed with a 1:1 by volume mixture of diethyl ether and petroleum ether (B.P. 40°-60°) to give the crude product (17.5 g.). Recrystallization from ethyl acetate/petroleum ether (B.P. 40°-60°) gave N-benzyloxycarbonyl-DL-2-(5-cyclopropylmethyl-2-pyrrolyl)glycine (14.0 g., 40%), M.P. 80°-85°. Found: C, 65.50; H, 6.18; N, 8.57. $C_{18}H_{20}N_2O_4$ requires: C, 65.84; H, 6.14; N, 8.53%. B. Dicyclohexylcarbodiimide (10 g.) was added to a stirred ice-cold solution of the N-protected amino acid from Part A, above, (11.5 g.) and N-hydroxy succinimide (5 g.) in dry methylene chloride (400 ml.). After stirring for 16 hours at 0° the reaction mixture was filtered and cold 10% (w/w) ethanolic ammonia (50 ml.) added to the filtrate. The solution was allowed to warm to room temperature and after a further 2½ hours the solution was evaporated to dryness. The residue was extracted with chloroform and the solution chromatographed on a column of silica eluting with chloroform followed by chloroform containing 5% methanol. The relevant fractions were combined and evaporated and the crude residue triturated with hot methanol to give DL-2-benzyloxycarbonylamino-2-(5-cyclopropylmethyl-2-pyrrolyl)acetamide (9.7 g., 84%). A sample was recrystallized from methanol, M.P. 184°-5°. Found: C, 65.90; H, 6.50; N, 12.81. $C_{18}H_{21}N_3O_3$ requires C, 66.04; H, 6.47; N, 12.84%. C. A solution of the product from Part B, above, (2.4 g.) in methanol (250 ml.) was hydrogenated over 10% palladium on charcoal catalyst (0.2 g.) for 6 hours at room temperature under a pressure of 3.2 kg./cm.$^2$ (45 p.s.i.). The mixture was filtered and evaporated to dryness.

The residue was extracted with ethyl acetate (10 ml.), filtered, and a solution of maleic acid (0.7 g.) in ethanol (10 ml.) was added. Dry diethyl ether (10 ml.) was added slowly, and the solution cooled to give DL-2-(5-cyclopropylmethyl-2-pyrrolyl)glycinamide maleate (0.9 g., 40%) as a white crystalline solid, M.P. 175° (decomp.). Found: C, 54.32; H, 6.09; N, 13.79. $C_{10}H_{15}N_3O \cdot C_4H_4O_4$ requires: C, 54.36; H, 6.19; N, 13.59%.

EXAMPLE 65

A. To a solution of N-benzyloxycarbonyl-DL-2-(5-cyclopropylmethyl-2-pyrrolyl)glycine (15 g.) in dry diethyl ether (100 ml.) at 0° was added excess diazomethane in diethyl ether. After one hour at 0° excess diazomethane was destroyed by adding acetic acid (3 ml.) in ether (30 ml.). The solution was filtered, concentrated to a volume of 50 ml. and filtered through a column of activated alumina (20 g.) eluting with a mixture of diethyl ether and ethyl acetate (4:1). The combined eluates were evaporated to yield an oil which was dissolved in methanol (200 ml.) and hydrogenated over 10% palladium on charcoal catalyst at room temperature and a pressure of 2.1 kg./cm.$^2$ (30 p.s.i.) until uptake was complete (3 hours). The catalyst was removed; by filtration and the solution evaporated to give an oil. The residue was dissolved in dry diethyl ether (20 ml.) and a slight excess of dry hydrogen chloride in diethyl ether added. Cooling to −30° precipitated the crude product as the hydrochloride salt (4 g., 35%). Recrystallization from acetonitrile containing a little ethyl acetate gave methyl DL-2-(5-cyclopropyl-methyl-2-pyrrolyl)glycinate hydrochloride, M.P. 128°-9°.

Found: C, 53.71; H, 7.01; N, 11.58. $C_{11}H_{16}N_2O_2 \cdot HCl$ requires: C, 53.98; H, 7.00; N, 11.45%.

B. The ester prepared in Part A, above, is dissolved in concentrated aqueous ammonia for several hours to give DL-2-(5-cyclopropylmethyl-2-pyrrolyl)glycinamide.

EXAMPLE 66

Employing the appropriate 2-substituted pyrrole starting material in place of 2-cyclopropylmethylpyrrole in procedure of Example 59 affords the following racemic amino acids.

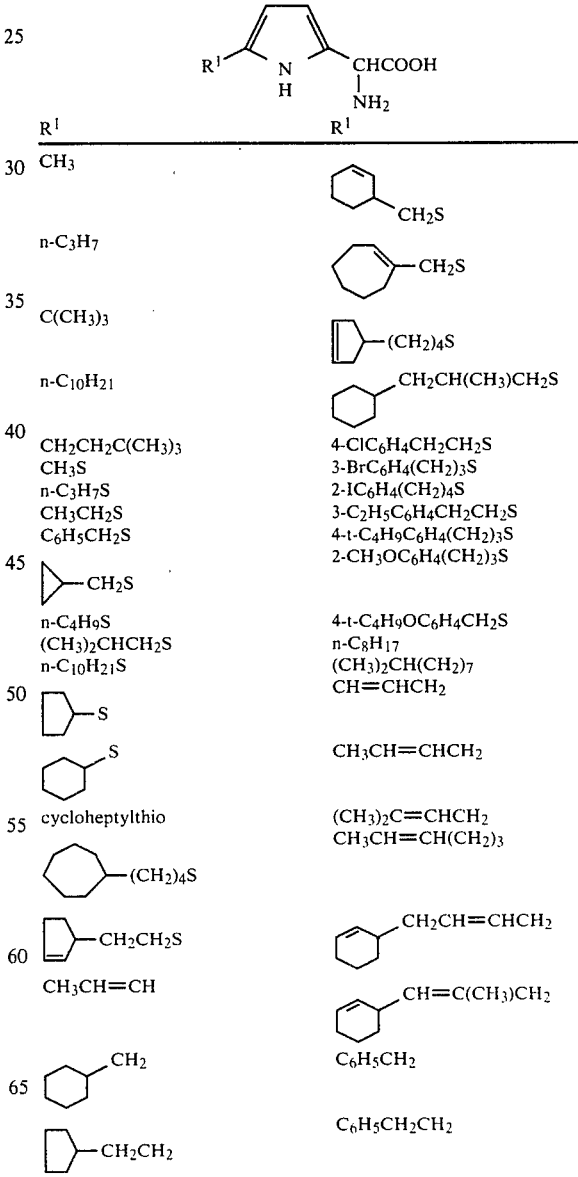

-continued

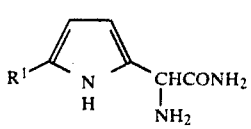

| R¹ | R¹ |
|---|---|
| ◁-CH₂ | 4-BrC₆H₄CH(CH₃)CH₂ |
| ○-CH₂CH₂ | 4-IC₆H₄CH₂CH₂ |
| ◁-CH₂CH₂ | 4-n-C₄H₉OC₆H₄CH₂ |
| ○-(CH₂)₃ | ○-CH=CH₂ |
| ○-(CH₂)₄ | ◁-C=CH \| CH₃ |
| cycloheptylmethyl | cycloheptylvinyl |
| ▷-(CH₂)₄ | ○-(CH₂)₂CH=CH |
| ◁-CH₂CH=CHCH₂ | ◁-CH=CH |
| ○-CH₂CH₂ | C₆H₅CH(CH₃)CH=CH |
| ○-CH₂ | 4-IC₆H₄CH=CH |
| 2-FC₆H₄CH₂ | 4-CH₃OC₆H₄CH=CH |
| 3-ClC₆H₄(CH₂)₄ | 4-n-C₄H₉OC₆H₄C=CH |
| 4-CH₃C₆H₄CH₂ | CH₃ |
|  | 3-CH₃C₆H₄(CH₂)₂CH=CH |
| ○-CH=CHCH₂ | 4-n-C₄H₉C₆H₄CH=CH |
| ○-CH(CH₃)CH₂ | ○-(CH₂)₂CH=CH |
| 3-FC₆H₄CH=CHCH₂ | |
| 4-CH₃OC₆H₄CH₂CH=CHCH₂ | ○-CH=CH |
| ○-CH=CHCH₂ | |
| n-C₄H₉ | |
| n-C₆H₁₃ | |
| CH₂CH(CH₃)₂ | |
| trans-4-ClC₆H₄CH=CH | |
| cis-4-ClC₆H₄CH=CH | |
| trans-4-(CH₃)₃CC₆H₄CH=CH | |

EXAMPLE 67

Employing the alpha-amino acid compounds provided in Examples 60, 61, 62, 63 and 66 as starting material in the procedure of Example 64 affords the corresponding DL-alpha-amino amides, of the formula below, in each case.

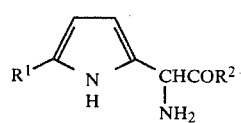

EXAMPLE 68

Treatment of the alpha-amino acids provided in Examples 60, 61, 62, 63 and 66 with benzylchloroformate by the procedure of Example 64 Part A, affords, in each case, the corresponding N-benzyloxycarbonylamino acid. The latter compounds are reacted with diazomethane by the procedure of Example 65, Part A to provide the corresponding methyl ester hydrochlorides.

EXAMPLE 69

Transesterification of the methyl esters provided in Example 68 with a 10–100-fold molar excess of an alcohol of formula ROH in the presence of sufficient potassium carbonate to maintain the reaction mixture at pH 5–8.5 and distilling off the methyl alcohol formed at reflux temperature, affords the corresponding ester of the following formula upon distillation of excess alcohol. Alternatively, the corresponding hydrochloride salt is obtained by cooling the reaction mixture and addition of an equimolar amount of dry hydrogen chloride gas,

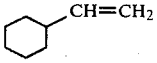

where $R^2$ is $OC_2H_5$, $OCH(CH_3)_2$, $OCH_2CH_2CH_3$, n-$C_4H_9O$, iso-$C_4H_9O$, sec-$C_4H_9O$ or t-$C_4H_9O$ and $R^1$ has one of the values assigned in Examples 60, 61, 62, 63 and 66.

EXAMPLE 70

Cationic Salt Formation 2-(5-n-Butyl-2-pyrrolyl)glyoxylic acid (1.95 g., 0.01 mole) is dissolved in 200 ml. of warm ethanol. An equivalent amount of alcoholic potassium hydroxide is added and the resulting mixture stirred for 15 minutes, then cooled. The precipitated potassium salt is filtered, washed with ethanol and dried in a vacuum oven. When aqueous sodium hydroxide, aqueous calcium hydroxide or alcoholic solutions of ammonia, or amines such as arginine, N-methyl-glucamine or choline are used in an equivalent amount in place of potassium hydroxide, the corresponding cationic salts are similarly obtained.

When 2-(5-n-butyl-2-pyrrolyl)glycine is used in place of the above glyoxylic acid in the above procedures, the corresponding cationic salts of this glycine derivative are provided.

When the remaining compounds of formula (I) wherein R is hydrogen or the remaining compounds of formula (II) wherein $R^2$ is OH are employed in the above procedures, the corresponding cationic salts are obtained in each case.

EXAMPLE 71

Acid Addition Salts of 5-Substituted-2-pyrrolylglycines

The method is exemplified as follows:
DL-2-(5-Cyclopropylmethyl-2-pyrrolyl)glycine (1.94 g., 0.01 mole) is warmed in sufficient ethanol to effect a solution. The mixture is cooled and an equivalent amount of alcoholic hydrochloric acid is added. The resulting mixture is evaporated to dryness and recrystallized to obtain the hydrochloride salt.

Hydrochloride salts of the remaining compounds of formula (II) are obtained in a similar manner.

When acids such as hydrobromic, sulfuric, phosphoric, acetic, maleic, fumaric, succinic, lactic, tartaric, citric, gluconic, saccharic or p-toluenesulfonic acid are used in place of hydrogen chloride in the above procedure, the corresponding acid addition salts are obtained in each case.

EXAMPLE 72

Parenteral Solutions

A. Glacial acetic acid (12.0 g.) and sodium acetate anhydrous (16.4 g.) are each dissolved in 1000 ml. of freshly distilled water to produce 0.2 molar solutions. 148.0 ml. of the acetic acid solution is then mixed with 352.0 ml. of the sodium acetate solution and the mixture made up to 1000 ml. with freshly distilled water. Sodium 2-(5-cyclopropylmethyl-2-pyrrolyl)glyoxylate monohydrate, 12 g., is then added and the resulting solution is then sterilized by filtration through a suitable bacteria-proof filter under aseptic conditions into sterile 50 ml. glass vials, which when filled with 30 ml. of the final solution, contain 300 mg. of the active ingredient, calculated as the acid.

B. Succinic acid (23.62 g.) and sodium hydroxide (98 g.) are each dissolved in 1000 ml. of freshly distilled water to produce 0.2 molar solutions. 250 ml. of the succinic acid solution is then mixed with 267.0 ml. of the sodium hydroxide and the mixture made up to 1000 ml. with freshly distilled water. DL-2-(5-cyclopropylmethyl-2-pyrrolyl)glycineamide, 10 g., is then added and the resulting 1% w/v solution is then sterilized as in Part A, above. Sterile 50 ml. glass vials, when filled with 40 ml. of the final solution, contain 400 mg. of the active ingredient.

EXAMPLE 73

The following are typical tablet or capsule formulations containing 2-(5-cyclopropylmethyl-2-pyrrolyl)-glyoxylic acid as active ingredient:

| | mg./tablet or capsule | | | | |
|---|---|---|---|---|---|
| | A | B | C | D | E |
| active ingredient | 500 | 100 | 100 | 25 | 25 |
| lactose | 30 | 170 | — | 220 | — |
| corn starch | 60 | 80 | — | 105 | — |
| microcrystalline cellulose ("Avicel")≠ | — | — | 170 | — | 220 |
| glycine | — | — | 80 | — | 105 |
| Fine silica ("Aerosil")≠ | — | 0.35 | 0.35 | 0.35 | 0.35 |
| Magnesium stearate* | 5 | 3 | 3 | 3 | 3 |
| | 595 | . . . | 353.35 | . . . | |

*9:1 blend with sodium lauryl sulphate.
≠ "Avicel" and "Aerosil" are Trademarks.

For formulations A, B, and D, the ingredients are thoroughly blended together, and then either filled directly into hard gelatin capsules of appropriate size, or granulated and compressed into tablets of the desired size. For formulations C and E, the ingredients are thoroughly blended together and slugged. The slugs are broken down into granules, and then either filled into capsules of the appropriate size, or directly compressed into tablets of the desired size.

In formulations A, B and D, the lactose may be replaced by equal amounts of calcium carbonate or dicalcium phosphate.

EXAMPLE 74

Example 73 is repeated using L- or DL-2-[5-(2-cyclohexyl)ethyl-2-pyrrolyl]glycine hydrochloride as active ingredient. Of course, twice as many capsules or tablets of this example may be required to be ingested for a single therapeutic administration when the racemic (DL) compound is employed.

PREPARATION 1

Cyclohexyl pyrrol-2-yl ketone

Methyl iodide (42.60 g.) in dry ether (150 ml.) was added to a stirred mixture of magnesium turnings (7.30 g.) in dry ether (50 ml.) at such a rate that gentle reflux was maintained. After completion of the addition the mixture was stirred at room temperature for 30 minutes and then pyrrole (20.13 g., 0.44 mole) was added at such a rate that gentle reflux was maintained. After completion of the addition the mixture was heated under reflux with stirring for 30 minutes and then cooled to 0° C. A solution of cyclohexane carboxylic acid chloride (44.0 g., 0.30 mole) in dry ether (100 ml.) was added dropwise with stirring and the resulting mixture was heated under reflux with stirring for 30 minutes. The mixture was cooled and a solution of ammonium chloride (20 g.) in water (200 ml.) was added with stirring. The organic layer was separated, washed once with 0.5 N sodium hydroxide solution (50 ml.), twice with water (100 ml.) and dried over sodium sulphate. The ether was evaporated to give a viscous oil which was distilled to give cyclohexyl pyrrol-2-yl ketone (31.5 g.), B.P. 162°–165° at 15 mm., M.P. 83°–84°.

Found: C, 74.5; H, 8.7; N, 7.8. $C_{11}H_{15}NO$ requires C, 74.5; H, 8.5; N, 7.9%.

PREPARATION 2

Cyclopentylmethyl pyrrol-2-yl-ketone

Pyrrole magnesium iodide was prepared from magnesium turnings (4.86 g.) methyl iodide (28.40 g.) and pyrrole (13.42 g.) in dry ether (200 ml.) as described in Preparation 1. To the stirred mixture was added a solution of ethyl cyclopentylacetate (31.2 g.) in dry ether (100 ml.) and the resulting mixture was heated under reflux with stirring for 3.5 hours, cooled and allowed to stand overnight.

A solution of ammonium chloride (14 g.) in water (100 ml.) was added, cautiously, with stirring and the organic layer was separated, washed twice with water (80 ml.) and dried over sodium sulphate. Evaporation of the ether gave an oil which was distilled to give cyclopentylmethyl pyrrol-2-yl ketone (14.2 g.) B.P. 162°–166° at 15 mm., M.P. 49°–51°.

Found: C, 74.2; H, 8.4; N, 7.8. $C_{11}H_{15}NO$ requires: C, 74.5; H, 8.5; N, 7.9%.

PREPARATION 3

2-Cyclohexylmethylpyrrole

A mixture of cyclohexyl pyrrol-2-yl ketone (17.7 g.) and 99% hydrazine hydrate (6.0 ml.) was heated under reflux in diethylene glycol (70 ml.) for 1.5 hours. The excess hydrazine hydrate and water were distilled off and the mixture was cooled. Potassium hydroxide (12.0 g.) was added portionwise and the mixture was then heated under reflux for 4 hours, cooled and poured into water (500 ml.). The mixture was extracted with ether (3×100 ml.) and the combined etheral extracts were washed with water (3×100 ml.) and dried over sodium sulphate. Evaporation of the ether gave an oil which was distilled to give 2-cyclohexylmethylpyrrole (11.3 g.), B.P. 137°–140° at 15 mm.

Found: C, 80.7; H, 10.3; N, 8.4. $C_{11}H_{17}N$ requires C, 80.9; H, 10.5; N, 8.6%.

Other 2-substituted pyrroles of the formula (III) prepared similarly are listed in the following table.

(III)

| $R^1$ | B.P. °C. | Analysis, Percent (Theoretical Figures in Brackets) | | |
|---|---|---|---|---|
| | | C | H | N |
| $CH_2$—▷ | 95–99/15 mm. | 78.93 (79.29 | 9.20 9.15 | 11.36 11.56) |
| $CH_2$—□ | 120–125/15 mm. | 79.64 (80.48 | 10.01 10.13 | 9.14 9.39) |
| $CH_2CH_2$—□ | 137–141/15 mm. | 81.19 (80.92 | 10.59 10.50 | 8.95 8.58) |
| $CH_2CH_2$—◇ | 134–136/15 mm. | 81.44 (81.93 | 9.40 9.38 | 8.63 8.69) |
| $CH_2CH_2$—○ | 110–114/2 mm. | 81.20 (81.29 | 10.79 10.80 | 8.37 7.90) |
| $CH_2CH_2C(CH_3)_3$ | 108–110/4 mm. | 78.68 (79.40 | 10.90 11.32 | 8.57 9.26) |

PREPARATION 4

By employing the appropriate carboxylic acid chloride in the procedure of Preparation 1 or carboxylic acid methyl or ethyl ester in the procedure of Preparation 2 and reduction of the product ketones by the procedure of Preparation 3, the following 2-substituted pyrroles are obtained in a like manner.

| $R^1$ | $R^1$ |
|---|---|
| ○—(CH₂)₃ | ○—CH=CHCH₂ |
| ○—(CH₂)₄ | ○—CHCH₂ / CH₃ |
| ○—CH₂ | ○—CH=CHCH₂ / F |
| □—CH(CH₃)CH₂ | CH₃O-C₆H₄-CH₂CH=CHCH₂ |
| ▷—(CH₂)₄ | ○—CH=CHCH₂ |

-continued

| $R^1$ | $R^1$ |
|---|---|
| □—CH₂CH=CHCH₂ | ○—CH₂CH=CHCH₂ |
| □—CH₂CH₂ | ○—CH=C(CH₃)CH₂ |
| ○—CH₂CH₂ | $C_6H_5CH_2CH_2$ |
| ○—CH=CHCH₂CH₂ | 4-$BrC_6H_4CH(CH_3)CH_2$ |
| ○—CH₂ | 4-$IC_6H_4CH_2CH_2$ |
| □—(CH₂)₄ | 4-n-$C_4H_9OC_6H_4CH_2$ |

2-$FC_6H_4CH_2$
3-$ClC_6H_4(CH_2)_4$
4-$CH_3C_6H_4CH_2$

PREPARATION 5 cis- and trans-2-[4-Chlorophenyl)vinyl]pyrrole

4-Chlorobenzyl triphenylphosphonium chloride (44.0 g., 0.104 mole) was added in portions to a stirred suspension of 50% sodium hydride-oil dispersion (5.0 g., 0.109 mole) in dry tetrahydrofuran (250 ml.) under nitrogen. The resulting yellow suspension was stirred at room temperature for 1 hour, then a solution of 2-formylpyrrole (9.9 g., 0.104 mole) in dry tetrahydrofuran (80 ml.) was added dropwise. The reaction mixture was stirred under reflux for 3 hours, and the solvent evaporated under vacuum. The residue was partitioned between ether and water; the ether phase was separated, dried ($MgSO_4$), concentrated, with chilling and filtered, to remove some triphenylphosphine oxide (6.8 g.).

The remaining ether solution was evaporated under vacuum and the residue dissolved in chloroform and chromatographed on silica gel with chloroform as eluent. The required fractions were combined and evaporated in vacuo to afford a pale green solid which was extracted with boiling hexane (200 ml.), cooled and filtered to furnish an off-white solid (5.8 g.), M.P. 172°. Further purification of a sample (0.50 g.) by column chromatography provided trans-2-[2-(4-chlorophenyl)-vinyl]pyrrole (0.36 g.), M.P. 174°–175°. (lit. M.P. 200°–201°).

The hexane filtrate was evaporated in vacuo to give, after trituration of the residue with hexane, an off-white solid (5.9 g.) which was further purified by column chromatography to afford cis-2-[2-(4-chlorophenyl)-vinyl]pyrrole (3.5 g.), M.P. 54°–55°.

Calculated for $C_{12}H_{10}ClN$: C, 70.76; H, 4.95; N, 6.88. Found: C, 70.40; H, 4.81; N, 6.89%.

trans-2-[2-(4-tert-Butylphenyl)vinyl]pyrrole was similarly prepared as described for the 4-chlorophenyl analogs. Column chromatography allowed a clean separation of the trans olefin which was crystallized from hexane as a grey solid, M.P. 118°–119°.

Found: C, 85.07; H, 8.58; N, 5.8. $C_{16}H_{19}N$ requires: C, 85.28; H, 8.50; N, 6.22%.

2-(2-Cyclopropylvinyl)pyrrole was similarly prepared, the product was obtained as a mixture of the cis and trans isomers in a ratio of 5:2 as judged by n.m.r. spectroscopy.

2-(Prop-1-enyl)pyrrole was similarly prepared. Chromatography of alumina gave the product as a red oil. The isomer ratio was not determined.

PREPARATION 6

2-(2-Cyclopropylethyl)pyrrole

A solution of cis-/trans-2-(2-cyclopropylvinyl)-pyrrole (1.7 g., 0.073 mole) in ethanol (100 ml.) was hydrogenated over 10% palladium on charcoal at room temperature and 3.5 kg./cm$^2$ (50 p.s.i.). The solution was filtered, the solvent evaporated and the residue distilled to give the required 2-(2-cyclopropylethyl)pyrrole as an oil (4.93 g.), B.P. 100°–103°./13 mm.

PREPARATION 7

By employing the appropriate Wittig reagent in place of 4-chlorobenzyl triphenylphosphonium chloride in the method of Preparation 5 the following 2-vinylpyrroles are obtained in like manner.

| $R^1$ | $R^1$ |
|---|---|
| cyclohexyl—CH=CH | 4-IC$_6$H$_4$CH=CH |
| cyclopropyl—C=CH, CH$_3$ | 4-CH$_3$OC$_6$H$_4$CH=CH |
| cyclopentyl—CH=CH | 4-n-C$_4$H$_9$OC$_6$H$_4$C=CH, CH$_3$ |
| cyclohexyl—CH$_2$CH$_2$CH=CH | 3-CH$_3$C$_6$H$_4$(CH$_2$)$_2$CH=CH |
| cyclopropyl—CH=CH | cyclohexyl—(CH$_2$)$_2$CH=CH |
| C$_6$H$_5$CHCH=CH, CH$_3$ | cycloheptyl—CH=CH |
|  | 4-n-C$_4$H$_9$C$_6$H$_4$CH=CH |

PREPARATION 8

Hydrogenation of the 2-olefinic pyrroles provided by the procedures of Preparations 3, 4, 5 and 7 by the method of Preparation 6 provides the corresponding hydrogenated compounds in each case.

We claim:

1. A compound of the formula $$R^1 \underset{H}{\overset{N}{\triangle}} CCO_2R \quad \| \quad O$$

and pharmaceutically acceptable cationic salts thereof, wherein R is hydrogen or alkyl having from one to four carbon atoms;

R$^1$ is a member selected from the group consisting of alkenyl having from three to six carbon atoms, cycloalkylthio having from five to seven carbon atoms and AR$^3$ where A is a member bonded to the pyrrole ring and is selected from the group consisting of alkylene and alkylenethio having from one to four carbon atoms, and alkenylene having from two to four carbon atoms and R$^3$ is a member selected from the group consisting of cycloalkyl having from three to seven carbon atoms, cycloalkenyl having from five to seven carbon atoms and C$_6$H$_4$R$^4$ where R$^4$ is a member selected from the group consisting of H, F, Cl, Br, I and alkyl and alkoxy having from one to four carbon atoms.

2. A compound according to claim 1 wherein R$^1$ is a member selected from the group consisting of cycloalkylmethyl having from three to six carbon atoms in said cycloalkyl group, 2-cyclohexylethyl and 2-cyclopentenylethyl.

3. A compound according to claim 1 wherein R$^1$ is 2-(cyclopent-2-enyl)ethyl.

4. A compound according to claim 1 wherein R$^1$ is cyclopropylmethyl.

5. A compound according to claim 1 wherein R$^1$ is 2-cyclohexylethyl.

6. A compound according to claim 1 wherein R$^1$ is cyclopentylmethyl.

7. The compound according to claim 1: 2-(5-cyclopropylmethyl-2-pyrrolyl)glyoxylic acid.

8. An L- or DL-compound of the formula $$R^1 \underset{H}{\overset{N}{\triangle}} CHCOR^2 \quad | \quad NH_2$$

and pharmaceutically acceptable cationic and acid addition salts thereof wherein R$^2$ is hydroxy, amino or alkoxy having from one to four carbon atoms;

R$^1$ is a member selected from the group consisting of alkenyl having from three to six carbon atoms, cycloalkylthio having from five to seven carbon atoms and AR$^3$ where A is a member bonded to the pyrrole ring and is selected from the group consisting of alkylene and alkylenethio having from one to four carbon atoms and alkenylene having from two to four carbon atoms and R$^3$ is a member selected from the group consisting of cycloalkyl having from three to seven carbon atoms, cycloalkenyl having from five to seven carbon atoms and C$_6$H$_4$R$^4$ where R$^4$ is a member selected from the group consisting of H, F, Cl, Br, I and alkyl and alkoxy having from one to four carbon atoms.

9. A compound according to claim 8 wherein R$^2$ is amino.

10. A compound according to claim 8 wherein R$^1$ is a member selected from the group consisting of cycloalkylmethyl having from three to six carbon atoms in said cycloalkyl group, 2-cyclohexylethyl and 2-cyclopentenylethyl.

11. A compound according to claim 10 wherein R$^1$ is 2-(cyclopent-2-enyl)ethyl.

12. A compound according to claim 10 wherein R$^1$ is cyclopropylmethyl.

13. A compound according to claim 10 wherein R$^1$ is 2-cyclohexylethyl.

14. A compound according to claim 10 wherein R$^1$ is cyclopentylmethyl.

15. A compound according to claim 8: 2-(5-cyclopropylmethyl-2-pyrrolyl)glycinamide.

16. A method of treating a mammalian subject suffering from a disease or condition attributable to reduced blood flow, reduced oxygen availability or reduced carbohydrate metabolism in the cardiovascular system which comprises orally or parenterally administering to said subject a cardiovascular blood flow, oxygen availability or carbohydrate metabolism increasing amount of a compound of the formula

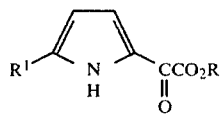

or a pharmaceutically acceptable cationic salt thereof, wherein R is hydrogen or alkyl having from one to four carbon atoms; and $R^1$ is a member selected from the group consisting of alkyl and alkylthio having from one to ten carbon atoms, alkenyl having from three to six carbon atoms, cycloalkylthio having from five to seven carbon atoms and $AR^3$ where A is a member bonded to the pyrrole ring and is selected from the group consisting of alkylene and alkylenethio having from one to four carbon atoms, and alkenylene having from two to four carbon atoms and $R^3$ is a member selected from the group consisting of cycloalkyl having from three to seven carbon atoms, cycloalkenyl having from five to seven carbon atoms and $C_6H_4R^4$ where $R^4$ is a member selected from the group consisting of H, F, Cl, Br, I and alkyl and alkoxy having from one to four carbon atoms.

17. A method of treating a mammalian subject suffering from a disease or condition attributable to reduced blood flow, reduced oxygen availability or reduced carbohydrate metabolism in the cardiovascular system which comprises orally or parenterally administering to said subject a cardiovascular blood flow, oxygen availability or carbohydrate metabolism increasing amount of a compound of a L- or DL-compound of the formula

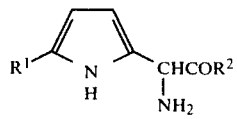

or a pharmaceutically acceptable cationic or acid addition salt thereof wherein $R^2$ is hydroxy, amino or alkoxy having from one to four carbon atoms; and $R^1$ is a member selected from the group consisting of alkyl and alkylthio having from one to ten carbon atoms, alkenyl having from three to six carbon atoms, cycloalkylthio having from five to seven carbon atoms and $AR^3$ wherein A is a member bonded to the pyrrole ring and is selected from the group consisting of alkylene and alkylenethio having from one to four carbon atoms and alkenylene having from two to four carbon atoms and $R^3$ is a member selected from a group consisting of cycloalkyl having from three to seven carbon atoms, cycloalkenyl having from five to seven carbon atoms and $C_6H_4R^4$ where $R^4$ is a member selected from the group consisting of H, F, Cl, Br, I and alkyl and alkoxy having from one to four carbon atoms.

18. The method according to claim 16 wherein said compound is 2-(5-cyclopropylmethyl-2-pyrrolyl)-glyoxylic acid.

19. The method according to claim 17 wherein said compound is 2-(5-cyclopropylmethyl-2-pyrrolyl)-glycinamide.

20. A pharmaceutical composition comprising a pharmaceutically acceptable carrier and a cardiovascular blood flow, oxygen availability or carbohydrate metabolism increasing amount of a compound of the formula

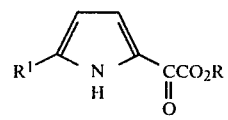

or a pharmaceutically acceptable cationic salt thereof, wherein R is hydrogen or alkyl having from one to four carbon atoms; and $R^1$ is a member selected from the group consisting of alkyl and alkylthio having from one to ten carbon atoms, alkenyl having from three to six carbon atoms, cycloalkylthio having from five to seven carbon atoms and $AR^3$ where A is a member bonded to the pyrrole ring and is selected from the group consisting of alkylene and alkylenethio having from one to four carbon atoms, and alkenylene having from two to four carbon atoms and $R^3$ is a member selected from the group consisting of cycloalkyl having from three to seven carbon atoms, cycloalkenyl having from five to seven carbon atoms and $C_6H_4R^4$ where $R^4$ is a member selected from the group consisting of H, F, Cl, Br, I and alkyl and alkoxy having from one to four carbon atoms.

21. A pharmaceutical composition comprising a pharmaceutically acceptable carrier and a cardiovascular blood flow, oxygen availability or carbohydrate metabolism increasing amount of a L- or DL-compound of the formula

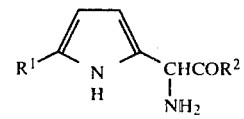

or a pharmaceutically acceptable cationic or acid addition salt thereof wherein $R^2$ is hydroxy, amino or alkoxy having from one to four carbon atoms; and $R^1$ is a member selected from the group consisting of alkyl and alkylthio having from one to ten carbon atoms, alkenyl having from three to six carbon atoms, cycloalkylthio having from five to seven carbon atoms and $AR^3$ where A is a member bonded to the pyrrole ring and is selected from the group consisting of alkylene and alkylenethio having from one to four carbon atoms and alkenylene having from two to four carbon atoms and $R^3$ is a member selected from the group consisting of cycloalkyl having from three to seven carbon atoms, cycloalkenyl having from five to seven carbon atoms and $C_6H_4R^4$ where $R^4$ is a member selected from the group consisting of H, F, Cl, Br, I and alkyl and alkoxy having from one to four carbon atoms.

* * * * *